United States Patent
Horstmann et al.

(10) Patent No.: US 6,207,183 B1
(45) Date of Patent: Mar. 27, 2001

(54) SURFACE-STABILIZED PHARMACEUTICAL PREPARATION FOR APPLICATION ON THE SKIN

(75) Inventors: Michael Horstmann, Neuwied; Wolfgang Laux, Dietz, both of (DE)

(73) Assignee: LTS Lohmann Therapie-Systeme AG (DE)

(*) Notice: Subject to any disclaimer, the term of this patent is extended or adjusted under 35 U.S.C. 154(b) by 0 days.

(21) Appl. No.: 09/091,259

(22) PCT Filed: Dec. 4, 1996

(86) PCT No.: PCT/EP96/05411

§ 371 Date: Jun. 8, 1998

§ 102(e) Date: Jun. 8, 1998

(87) PCT Pub. No.: WO97/21430

PCT Pub. Date: Jun. 19, 1997

(30) Foreign Application Priority Data

Dec. 9, 1995 (DE) ............................. 195 46 024

(51) Int. Cl.⁷ ............................. A61F 13/02; A61K 9/70; A61L 15/16

(52) U.S. Cl. ............................. 424/448; 424/449

(58) Field of Search ............................. 424/448, 449

(56) References Cited

U.S. PATENT DOCUMENTS

| | | | |
|---|---|---|---|
| 5,536,263 | * 7/1996 | Rolf et al. | 604/307 |
| 5,770,220 | * 6/1998 | Meconi et al. | 424/448 |
| 5,820,875 | * 10/1998 | Fallon | 424/448 |

FOREIGN PATENT DOCUMENTS

| | | | |
|---|---|---|---|
| 0366244 | 3/1993 | (EP) | G01R/13/20 |
| 0402407 | 3/1994 | (EP) | A61L/15/16 |

\* cited by examiner

*Primary Examiner*—Thurman K. Page
*Assistant Examiner*—S. Howard
(74) *Attorney, Agent, or Firm*—D. Peter Hochberg; Katherine R. Vieyra; William H. Holt

(57) ABSTRACT

An active substance-containing transdermal pharmaceutical preparation with a given size of contact surface, comprising a tack-free backing layer which is permeable to active substances and an adhesive layer adhering to the skin is characterized by the fact that the backing layer comprises at least a third of the total active substance amount contained in the preparation.

11 Claims, 1 Drawing Sheet

SURFACE-STABILIZED PHARMACEUTICAL PREPARATION FOR APPLICATION ON THE SKIN

The present invention relates to a pharmaceutical preparation for the release of active substances through the skin into the human body.

Since the Middle Ages, it has been known that pharmaceutical active substances migrate through human skin, and that applying or spreading adequate pharmaceutical active substance preparations on the skin can therefore cause medicinal effects. These effects are not limited to the skin and the underlying tissue; they may reach distant organs when suitable substances are used, because the active substances are distributed via the blood circulation after absorption. For example, hormone-containing ointments and creams are on the market today. Moreover, antirheumatic semisolid preparations are commercially available; after spreading them onto the skin they develop a therapeutic action via local or systemic effects. In this connection, the degree of active substance absorption is determined not only by the active substance concentration, but also—among other things—by the difficultly controllable size of the treated skin area. Also, the user can hardly control the layer thickness of the applied preparation precisely, which is contributory to the therapeutic result. For this reason therapeutic measures using these forms involve unacceptable deficiencies.

Transdermal therapeutic systems (TTSs) which, in addition to the active substance concentration, also exactly define the application surface do not have this disadvantage. The currently known TTSs have several basic things in common:

1. A tack-free backing layer which is impermeable to the components of the TTS is used for protection from undesired release of volatile TTS components to the environment, for protection from disadvantageous effects on contact with other surfaces, and, not least, to ensure mechanical stability of the TTS.

2. Since TTSs are to adhere intimately to the skin, the layer which faces the skin is rendered self-adhesive, at least partially.

3. Because of these self-adhesive properties a removable protective layer which has been rendered anti-adherent is applied for storage purposes prior to use.

In general, the backing layer consists of suitable materials, such as plastic films; but papers, nonwovens, or textiles are also suitable.

Despite the progress achieved, the above-mentioned TTSs may also have some disadvantages. For example, a backing layer which is impermeable to active substances and whose surface has been stabilized impairs patients' feeling of wearing comfort. The rigidity of the films used may result in undesired area limitations. Since some pharmaceutical active substances may have a relatively low transport rate through the skin in relation to the surface, a larger system surface is desirable to provide sufficient effective TTSs also for these active substances.

There have been several attempts of improving the wearing comfort by using elastic materials for the backing layer (e.g., U.S. Pat. No. 5,246,705); however, a restriction to materials which are impermeable to the medicinal agents has expressly been made. Another disadvantage of prior art TTSs is their thickness which patients sometimes find disagreeable. In conventional designs only the matrix, adhesive layer, or optional reservoir layers are mainly used to store and release the active substance, for this reason a backing layer which, according to definition, is impermeable to active substances is of no function in this respect.

It is the object of the present invention to provide a pharmaceutical preparation adhering to the skin with a given size of contact surface, comprising a tack-free backing layer and an active substance-containing reservoir formed of a skin-adherent adhesive layer, and not having the drawbacks of the state of the art.

According to the present invention this object is achieved by the fact that the backing layer comprises at least a third of the total active substance amount contained in the preparation. Including the backing layer in the diffusion process, advantageously results in the fact that it has two functions in the system according to the present invention: On the one hand, it forms part of the active substance reservoir, and on the other hand it is a backing layer preventing the patch from sticking to textiles or other articles. Most surprisingly, it was found that the unavoidable active substance permeability is not disadvantageous in general, since only volatile active substances and/or auxiliary agents result in a noticeable loss via the backing layer to the environment.

Examples of such pharmaceutical active substances include nicotine and nitroglycerin. Ethanol, propanediol, and other low-molecular alcohols, menthol, eucalyptol, limonene, and many other terpenes, low-molecular fatty acids, such as, capric acid, dimethyl sulfoxide are examples of typical additives in such preparations which, to a greater or lesser extent, emerge from the preparation through the backing layer. Unexpectedly, a widespread reservation (e.g., EP 0 366 240, p. 3, I. 24; or EP 0 402 407, p. 5, I. 4) with respect to a backing layer that is permeable to active substances turned out to be essentially unfounded, since the active substance amount migrating from the backing layer via the adhesive layer to the skin is by far larger than that migrating to the outside.

Owing to the small thickness and the possibility of using very flexible materials as base materials for the backing layer, the preparations according to the present invention, in addition to their different functionality, clearly differ in appearance from other TTSs of classical design. Since the preparation follows fine skin wrinkles, there is the impression of a thin layer present on the skin as opposed to a rigid adhesive film. In this respect, the subject matter of the present invention is an intermediate between a TTS and an ointment applied to an area of the skin.

A production method wherein a substantial portion of the active substance is introduced into the backing layer already during manufacture avoids migration processes which probably result in fold formation owing to swelling.

Numerous materials are suitable for such a backing layer, some examples are: polyvinyl alcohol, styrene-diene block copolymers, polyurethanes, polyvinyl chloride, polymethacrylates, and many other substances are basically suitable.

In an advantageous embodiment, the backing layer is covered by a supporting layer which is removable after application; this adheres to the whole surface thereof and has been rendered anti-adherent. Pharmaceutical active substances which may advantageously be used include steroid hormones, active substances having an effect on the central nervous system or on the Alzheimer's disease, antirheumatics, or acetylsalicylic acid.

EXAMPLES

Example 1

A) 10 g styrene-isoprene-styrene copolymer (Cariflex® TR 1107) is completely dissolved in 20 g naphtha having a boiling range between 80 and 100° C.

100 mg 17-β-estradiol, dissolved in 5 g ethyl acetate, is added; the mass is mixed homogeneously and, using a gap width of about 150 μm, coated on an antiadhesive polyester film such that a uniform layer having a weight per unit area of 30 g/m² results after drying for 4 hours at 35° C.

B) In a separate operation, a solution of 20 g hydrogenated colophony glycerol ester resin (Staybelite Ester® 5E) and 8 g styrene-isoprene-styrene copolymer (Cariflex® TR 1107) is prepared in 10 g ethyl acetate and 10 g naphtha having a boiling range between 80 and 100° C.; 0.12 g 17-β-estradiol is added which dissolves completely at room temperature. Using a gap width of about 100 μm, the mass is coated on an antiadhesive polyester film such that a uniform layer having a weight per unit area of 23 g/m² results after drying for 30 minutes at 35° C. and afterdrying for 15 minutes at 60° C.

The so produced layers of phase A (backing layer) and phase B (reservoir) are laminated on top of each other and spontaneously form a composite which cannot be separated manually. The anti-adhesive polyester film of phase B and the adhesive layer as well as the backing layer are punched into a contour corresponding to the geometric form of the preparation in a manner known to the skilled artisan, and the external residues are removed. Each administration form is packed into an individual sealed bag.

The user takes the drug from the package, removes the protective layer (release liner) from the adhesive layer, sticks the administration form onto a suitable site of the skin, and finally removes from the backing layer the polyester film rendered anti-adherent and used as supporting layer.

In the following, the structure of a preparation according to the present invention will be illustrated in greater detail with reference to embodiment examples according to FIGS. 1 to 3.

Figure 1:
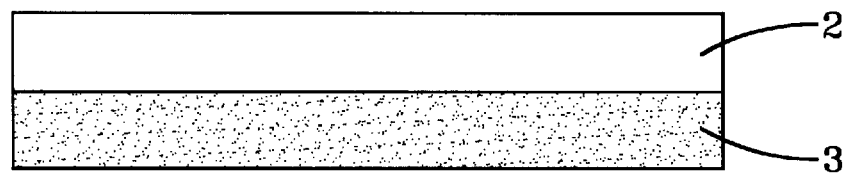
FIG. 1 shows a sectional view of the basic construction of the transdermal patch comprising the active substance-containing backing layer (2) which is permeable to active substances and the active substance-containing reservoir formed with an adhesive layer (3).
Figure 2:
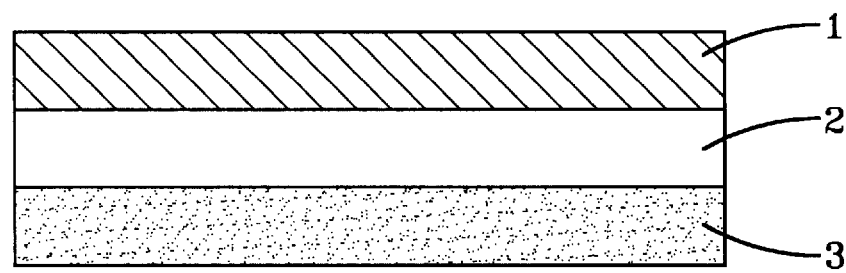
FIG. 2 shows the patch according to FIG. 1, however, with the supporting layer (1) completely adhering to the backing layer (2).
Figure 3:
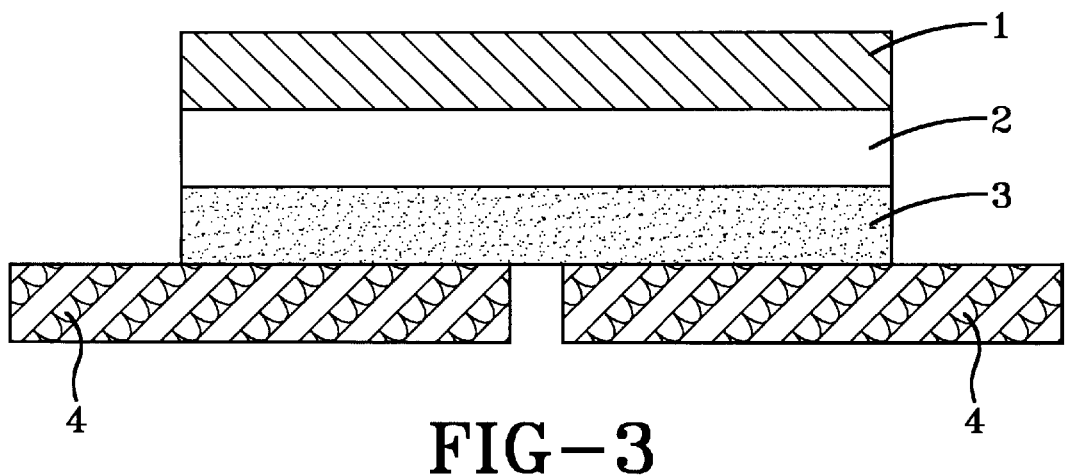
FIG. 3 shows the patch according to FIGS. 1 and 2, however, the adhesive layer (3) is additionally completely covered with a non-stick, removable supporting layer (4) (release liner) for the adhesive layer (3).

What is claimed is:

1. An active substance-containing transdermal pharmaceutical preparation with a given size of contact surface, comprising a tack-free backing layer which is permeable to active substances and comprises at least a third of the total active substance in the transdermal pharmaceutical preparation, and an adhesive layer for adhering the transdermal pharmaceutical preparation to the skin.

2. The pharmaceutical preparation according to claim 1 characterized in that the backing layer is covered by a supporting layer which adheres to the whole surface thereof, has been rendered antiadhesive, and is removable after application.

3. The pharmaceutical preparation according to claim 1 or 2 characterized in that the adhesive layer is covered by a nonstick protective layer which adheres to the whole surface thereof and is removable prior to application to the skin.

4. The pharmaceutical preparation according to one or several of the preceding claims characterized in that the adhesive layer and the backing layer together have a thickness of less than 80 μm.

5. The pharmaceutical preparation according to one or several of the preceding claims characterized in that it comprises a steroid hormone as pharmaceutical active substance.

6. The pharmaceutical preparation according to one or several of claims 1 to 4 characterized in that it comprises as pharmaceutical active substance one having an effect on the central nervous system.

7. The pharmaceutical preparation according to one or several of claims 1 to 4 characterized in that it comprises as pharmaceutical active substance one having an effect on the Alzheimer's disease.

8. The pharmaceutical preparation according to one or several of claims 1 to 4 characterized in that it comprises an antirheumatic as pharmaceutical active substance.

9. The pharmaceutical preparation according to one or several of claims 1 to 4 characterized in that it comprises acetylsalicylic acid as pharmaceutical active substance.

10. A process for the production of a transdermal pharmaceutical preparation according to the preceding claims, characterized in that, in a first step, a polymer used as base material is brought into solution by adding solvents or is made into a melt by heating, at least a third of the intended active substance amount is added and homogeneously mixed, the anti-adhesive supporting film is coated with the mixture to form a uniform layer which is dried, and that, in a separate step, a spreadable adhesive mass comprising the remaining active substance amount is also coated on the anti-adhesive protective film and dried, that the layers so produced are laminated on top of each other, and that patches are formed by punching.

11. The pharmaceutical preparation according to claim 1, wherein the remaining active substance amount is provided in the adhesive layer.

* * * * *